(12) United States Patent
Agouridas et al.

(10) Patent No.: US 7,119,180 B2
(45) Date of Patent: Oct. 10, 2006

(54) 2-HALOGENATED DERIVATIVES OF 5-O-DESOSAMINYL-ERYTHRONOLIDE A, THEIR PREPARATION PROCESS AND THEIR ANTIBIOTIC USE

(75) Inventors: Constantin Agouridas, Nogent sur Marne (FR); Francois Bretin, Ozoir la Feriere (FR); Alexis Denis, Paris (FR); Claude Fromentin, Paris (FR)

(73) Assignee: Aventis Pharma S.A., Antony (FR)

( * ) Notice: Subject to any disclaimer, the term of this patent is extended or adjusted under 35 U.S.C. 154(b) by 2 days.

(21) Appl. No.: 10/987,402

(22) Filed: Nov. 12, 2004

(65) Prior Publication Data

US 2005/0065101 A1  Mar. 24, 2005

Related U.S. Application Data

(63) Continuation of application No. 10/075,635, filed on Feb. 13, 2002, now abandoned, which is a continuation of application No. 09/416,022, filed on Oct. 8, 1999, now Pat. No. 6,352,983.

(30) Foreign Application Priority Data

Oct. 15, 1998 (FR) .................................. 98 12937

(51) Int. Cl.
   *C07H 17/08* (2006.01)
   *C07D 243/00* (2006.01)
   *C07D 498/00* (2006.01)

(52) U.S. Cl. ...................... 536/7.4; 540/556

(58) Field of Classification Search ............... 536/7.4; 540/556
   See application file for complete search history.

(56) References Cited

FOREIGN PATENT DOCUMENTS

| EP | 0487411 | 5/1992 |
|----|---------|--------|
| FR | 2742757 | 6/1997 |
| WO | WO 99/21871 | 5/1999 |

*Primary Examiner*—Brenda Coleman
(74) *Attorney, Agent, or Firm*—Balaram Gupta

(57) ABSTRACT

A subject of the invention is a process for the preparation of the compounds of formula (I):

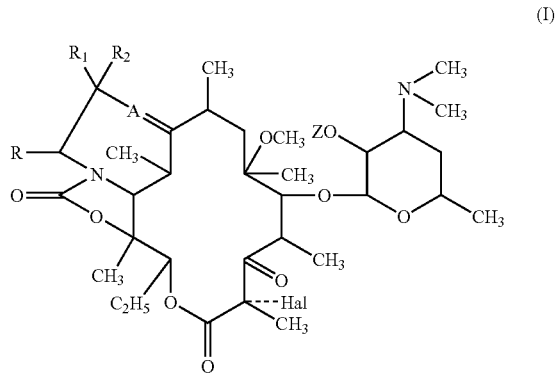

Wherein the substituents are defined as in the application. The compounds of this invention exhibit antibiotic properties.

7 Claims, No Drawings

2-HALOGENATED DERIVATIVES OF 5-O-DESOSAMINYL-ERYTHRONOLIDE A, THEIR PREPARATION PROCESS AND THEIR ANTIBIOTIC USE

This application is a continuation of U.S. application Ser. No. 10/075,635, filed Feb. 13, 2002, now abandoned, which is a continuation of U.S. application Ser. No. 09/416,022, filed Oct. 8, 1999, now U.S. Pat. No. 6,352,983 B1, issued, Mar. 5, 2002; which claims the benefit of priority of French Patent Application No. 98/12,937, filed Oct. 15, 1998, all of which are incorporated herein by reference in their entirety.

BACKGROUND OF THE INVENTION

Field of the Invention

The present invention relates to new 2-halogenated derivatives of 5-O-desosaminylerythronolide A, their preparation process and their use as medicaments. More particularly, this invention relates to processes for the preparation of 2-halogenated derivatives of 5-O-desosaminylerythronolide A

SUMMARY OF THE INVENTION

This invention provides a process for the preparation of novel 2-halogenated derivatives of 5-O-desosaminylerythronolide A.

OBJECTS OF THE INVENTION

It is an object of the invention to provide the novel compounds of formula I and their acid addition salts and a process for their preparation.

It is another object of the invention to provide novel antibiotic compositions and a method of treating bacterial infections in warm-blooded animals.

These and other objects and advantages of the invention will become obvious from the following detailed description.

DETAILED DESCRIPTION OF THE INVENTION

The novel products of the invention are compounds selected from the group consisting of a compound of formula I:

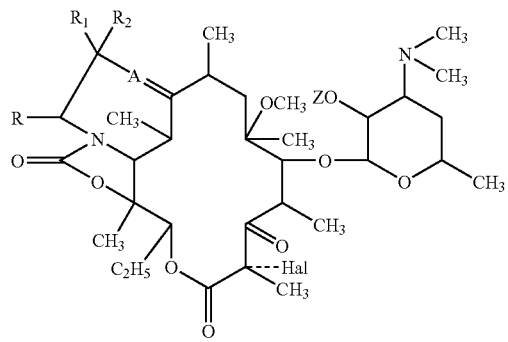

(I)

wherein A is nitrogen or N→O, $R_1$ and $R_2$ are individually selected from the group consisting of hydrogen and alkyl of 1 to 18 carbon atoms, R is selected from the group consisting of hydrogen and —$(CH_2)_m$OB, m is an integer from 1 to 8 and B is a hydrogen or

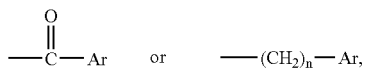

n is an integer from 1 to 8 and Ar is a mono- or polycyclic aryl or heteroaryl, Hal is halogen, and Z is hydrogen or acyl of an organic carboxylic acid of up to 18 carbon atoms, and its non-toxic, pharmaceutically acceptable acid addition salts.

Examples of acids for the acid addition salts are acetic acid, propionic acid, trifluoroacetic acid, maleic acid, tartaric acid, methanesulfonic acid, benzenesulfonic acid, p-toluenesulfonic acid and particularly stearic acid, ethylsuccinic acid or laurylsulfonic acid.

Examples of alkyl are methyl, ethyl, propyl, isopropyl, n-butyl, isobutyl, terbutyl, decyl and dodecyl.

Examples of aryl are phenyl or naphthyl and examples of heteroaryl are thienyl, furyl, pyrolyl, thiazolyl, oxazolyl, imidazolyl, thiadiazolyl, pyrazolyl or isopyrazolyl, pyridyl, pyrimidyl, pyridazinyl and pyrazinyl and also indolyl, benzofuranyl, benzothiazolyl and quinolinyl.

Examples of substituents are at least one of hydroxyl, halogen, $NO_2$, —CN, alkyl, alkenyl or alkynyl, O-alkyl, O-alkenyl or O-alkynyl, S-alkyl, S-alkenyl or S-alkynyl and N-alkyl, N-alkenyl or N-alkynyl of up to 12 carbon atoms optionally substituted by at least one halogen,

wherein $R_a$ and $R_b$ individually being hydrogen or alkyl of up to 12 carbon atoms,

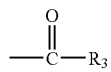

wherein $R_3$ being alkyl of up to 12 carbon atoms, or an optionally substituted aryl or heteroaryl radical, carbocyclic aryl, O-aryl or S-aryl, or heterocyclic aryl, O-aryl or S-aryl with 5 or 6 members comprising at least one heteroatom, optionally substituted by one or more of the above substituents.

Hal is halogen, preferably fluorine or chlorine. When one of the substituents is halogen, it is preferably fluorine, chlorine or bromine.

Among the preferred compounds of formula I are those wherein $R_1$ and $R_2$ are hydrogen, those wherein A is nitrogen, those wherein Hal is fluorine, those wherein R is hydrogen, and those wherein R is —$CH_2OH$.

The process for the preparation of a compound of formula I comprises a compound of the formula II:

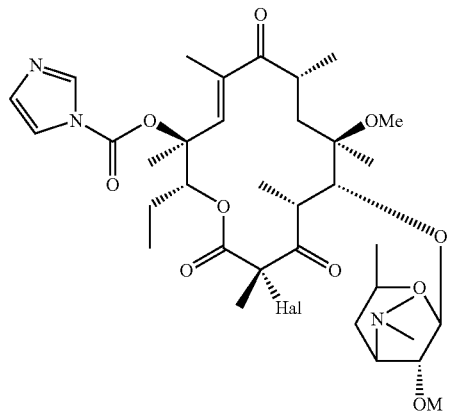

wherein Hal is halogen and OM is a protected hydroxyl is reacted with a compound of the formula III:

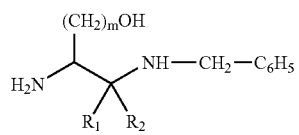

wherein m is an integer from 1 to 8 to obtain a compound of the formula IV:

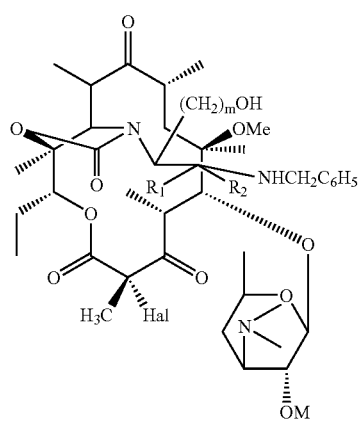

deprotecting the 2'-hydroxyl to obtain a compound of the formula V:

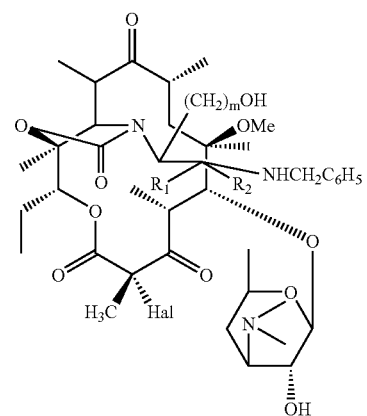

reacting the latter with a debenzylating agent to obtain a compound of the formula VI:

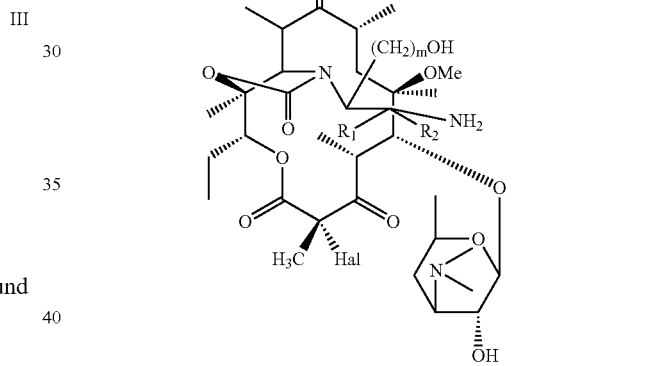

reacting the latter with a cyclization agent to form a compound of the formula IA:

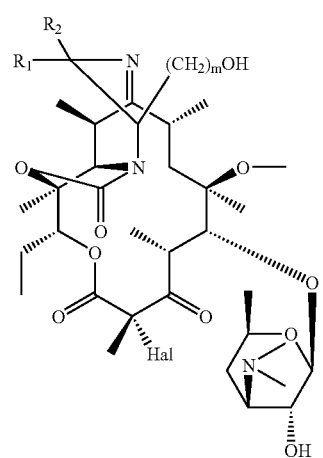

wherein R is a —(CH$_2$)$_m$OH and optionally subjecting the latter to aralkylating or acylating agent to obtain a compound of claim 1 wherein B is —(CH$_2$)$_n$Ar or

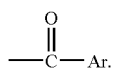

The starting compounds of formula II are described in French Patent Application 98/04,366, filed Apr. 8, 1998 and a detailed description of the process for the preparation of compounds of formula II wherein Hal is fluorine is described herein.

The process comprises reacting a compound of the formula A:

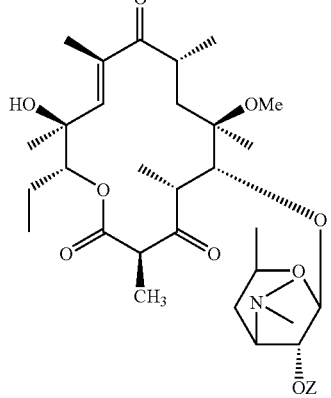

wherein —OZ is —OH or a protected hydroxyl with a fluorination agent to obtain a compound of the formula B:

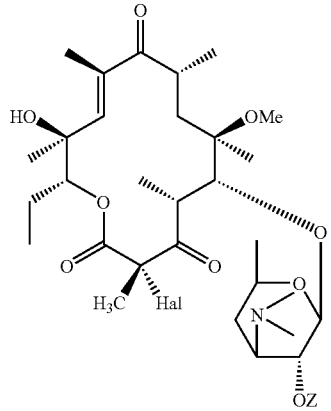

which is then reacted with 1,1'-carbonyldiimidazole, to obtain the compound of formula II. Other products can be prepared in an analogous manner.

Preferably, OZ is acetyl or benzyl and the protected hydroxyl can be released by methanolysis. The debenzylation may be effected by hydrogenation such as with palladium on carbon in the presence of ammonium formate at methanol reflux and cyclization may be effected at ethanol reflux in the presence of acetic acid. The acylation or arylation can be carried out by standard procedures.

The compounds of formulae IV, V and VI are novel and are part of the invention.

In a variation of the process to prepare the compounds of formula I, a compound of the formula IIIA:

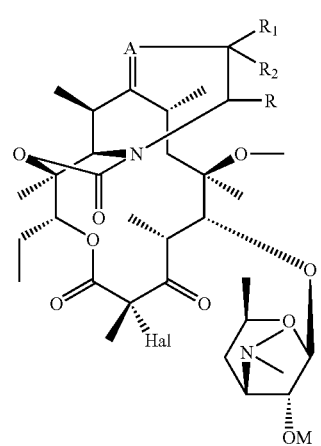

wherein A, R, R$_1$ and R$_2$ are defined as above and —OM is a protected hydroxyl is reacted with a halogenation agent to obtain a compound of the formula IB:

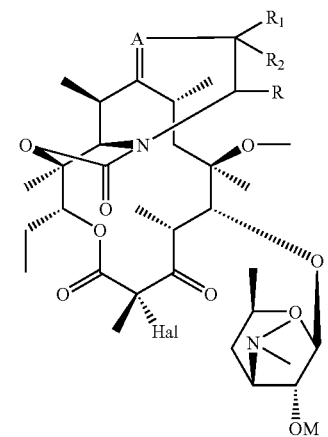

which is optionally reacted with an agent to free the 2'-hydroxyl to obtain the compound of formula I wherein Z is hydrogen and optionally reacted with an esterification agent to obtain 2'-acylated compound or with an acid to form the acid addition salt.

The preferred halogenation agent is bisphenyl sulfonylimide of the Formula:

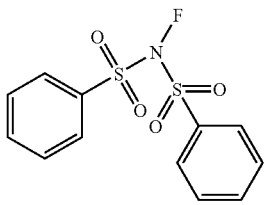

The novel antibiotic compositions of the invention are comprised of an antibiotically effective amount of a compound of formula I and its non-toxic, pharmaceutically acceptable acid addition salts and an inert pharmaceutical carrier. The compositions may be in the form of plain or sugar-coated tablets, gelatin capsules, granules, suppositories, injectable preparations, ointments, creams, gels.

Examples of the pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions can also be present in the form of a powder intended to be dissolved extemporaneously in an appropriate vehicle, for example, apyrogenic sterile water.

The compositions have a very good antibiotic activity on gram+bacteria such as staphylococcis, streptococcis, pneumococcis and therefore are useful in the treatment of germ-sensitive infections and particularly in that of staphylococcia such as staphylococcal septicaemias, malignant staphylococcia of the face or skin, pyodermitis, septic or suppurant wounds, boils, anthrax, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as pneumonia, bronchitis; brucellosis, diphtheria, gonococcal infection.

The compositions are also active against infections caused by germs such as *Haemophilus influenzae, Rickettsia, Mycoplasma pneumoniae, Chlamydia, Legionella, Ureaplasma, Toxoplasma*, or germs of the *Mycobacterium* genus.

The method of treating bacterial infections in warm-blooded animals comprises administering to a warm-blooded animal an antibiotically effective amount of a compound of formula I or its acid addition salt. The compounds can be administered buccally, rectally, parenterally or by topical application on the skin and mucous membranes, but the preferred administration route is the buccal route. The usual effective daily dose is 2 to 15 mg/kg depending on the method of administration and the active compound.

In the following examples, there are described various preferred embodiments to illustrate the invention. However, it is to be understood that the invention is not intended to be limited to the specific embodiments.

EXAMPLE 1

[3 as-(3aR*,4S*,7R*,9S*,10S*,11S*,13S*,15S*, 15aS*)]-4-ethyl-7-fluoro-3a,4,10,11,12,13,15,15a-octahydro-11-methoxy-3a,7,9,11,13,15-hexamethyl-10-[[3,4,6-trideoxy-3-(dimethyl-amino)-beta-D-xylo-hexopyranosyl]oxy]-14,1-(nitriloethano)-2H-oxacyclotetradecino[4,3-d]oxazole-2,6,8(9H)-trione Stage A: [3aS-(3aR*,4S*,7S*,9S*,10S*,11S*,13S*,15S*, 15aS*)]-4-ethyl-3a,4,10,11,12,13,15,15a-octahydro-11-methoxy-3a,7,9,11,13,15-hexamethyl-10-[[3,4,6-trideoxy-3-(dimethylamino)-2-O-(trimethylsilyl)-beta-D-xylo-hexopyranosyl]oxy]-14,1-(nitriloethano)-2H-oxacyclotetradecino[4,3-d]oxazole-2,6,8(7H,9H)-trione.

A mixture of 0.9835 g of [3aS-(3aR*,4S*,7S*,9S*,10S*, 11S*,13S*,15S*,15aS*)]-4-ethyl-3a,4,10,11,12,13,15,15a-octahydro-11-methoxy-3a,7,9,11,13,15-hexamethyl-10-[[3, 4,6-trideoxy-3-(dimethyl-amino)-beta-D-xylo-hexopyranosyl]oxy]-14,1-(nitriloethano)-2H-oxacyclotetradecino[4,3-d]oxazole-2,6,8(7H,9H)-trione (EP 0 638 585) and 9.8 ml of THF were stirred for 5 minutes and then 105 mg of imidazole and 0.327 ml of hexamethylsilylamine [(CH$_3$)$_3$Si]$_2$NH were added. The mixture was stirred for 5 days during which twice 0.2 eq of 3-pyrazolamine and twice 0.2 eq of hexamethylsilylamine were added followed by drying and taking up in methylene chloride. 30 ml of a solution of sodium dihydrogen phosphate were added and the mixture was stirred for 15 minutes followed by decanting. The aqueous phase was extracted with methylene chloride and the chloromethylenic phases were combined, dried, filtered and evaporated to obtain 1.2259 g of desired product.

Stage B: [3aS-(3aR*,4S*,7S*,9S*,10S*,11S*,13S*,15S*, 15aS*)]-4-ethyl-7-fluoro-3a,4,10,11,12,13,15,15a-octahydro-11-methoxy-3a,7,9,11,13,15-hexamethyl-10-[[3,4,6-trideoxy-3-(dimethylamino)-2-O-(trimethylsilyl)-beta-D-xylo-hexopyranosyl]oxy]-14,1-(nitriloethano)-2H-oxacyclotetradecino[4,3-d]oxazole-2,6,8(7H,9H)-trione A solution of 1.1003 g of the product of Stage A and 11 ml of THF was cooled to −10° C. and 1.86 ml of potassium terbutylate in THF were added. The mixture was stirred for 5 minutes and 0.588 g of

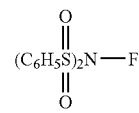

were added. The mixture was stirred for 10 minutes at −10° C. and the reaction medium was allowed to return to ambient temperature. The mixture was stirred at ambient temperature for 1 hour 30 minutes followed by filtration. The precipitate was rinsed with ethyl acetate and the filtrate was concentrated and taken up in 10 ml of ethyl acetate, 10 ml of water and 5 ml of a 20% aqueous solution of ammonium hydroxide. The mixture was stirred for 10 minutes followed by decanting, washing with water and extracting with ethyl acetate. The organic phases were combined, dried, filtered and evaporated to dryness to obtain 1.1067 g of the desired product.

Stage C: [3aS-(3aR*,4S*,7R*,9S*,10S*,11S*,13S*,15S*, 15aS*)]-4-ethyl-7-fluoro-3a,4.10.11.12.13.15.15a-octahydro-11-methoxy-3a,7.9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2.6,8(9H)-trione 1.13 ml of a solution of tetrabutylammonium fluoride in THF were added to a solution containing 0.55 g of the product of Stage A and 5.5 ml of THF and the mixture was stirred for 4 hours 30 minutes. The solvent was evaporated off and the residue was taken up in 5 ml of ethyl acetate, 5 ml of water and 2 ml of a 20% solution of ammonium hydroxide. The mixture was stirred for 15 minutes followed by decanting. The aqueous phase was extracted with ethyl acetate followed by washing with water. The aqueous phase was re-extracted and the organic phases were combined, dried, filtered and evaporated to dryness to obtain 0.4134 g of the desired product.

EXAMPLE 2

(3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2,6,8(7H,9H)-trione Stage A: 11,12-dideoxy-3-de[(2,6-dideoxy-3-C-methyl-3-O-methyl-.alpha.-L-ribo-hexopyranosyl)oxy]-2-fluoro-6-O-methyl-3-oxo-12,11-[oxycarbonyl[[(2R)-1-hydroxy-3-[(phenylmethyl) amino]-2-propyl]imino]-2'-acetoxy 6.7 g of the product of Preparation I were introduced into a solution containing 8.33 g of (R)-2-amino-3-[(phenylmethyl)amino]-1-propanol, 67 ml of acetonitrile and 6.7 ml of water and after the reaction mixture was taken to 55° C., it was maintained at this temperature for 21 hours. The reaction mixture was then poured into a water-ethyl acetate mixture followed by decanting, extracting with ethyl acetate, drying, filtering and evaporating to obtain 10.7 g of the desired product.

Stage B: 11,12-dideoxy-3-de[(2,6-dideoxy-3-C-methyl-3-O-methyl-.alpha.-L-ribo-hexopyranosyl)oxy]-2-fluoro-6-O-methyl-3-oxo-12,11-[oxycarbonyl[[(2R)-1-hydroxy-3-[(phenylmethyl) amino]-2-propyl]imino]-erythromycin 107 ml of methanol were added to 10.7 g of the product of Stage A and the mixture was stirred for 15 hours at ambient temperature. The methanol was evaporated off followed by drying to obtain 9.47 g of the desired crude product which was purified by two successive chromatographic elutions; first eluting with a methylene chloride/methanol/ammonium hydroxide mixture (96/4/0.4), and then eluting with an ethyl acetate/triethylamine mixture to obtain 2.66 g of the desired product.

Stage C: 11,12-dideoxy-3-de[(2,6-dideoxy-3-C-methyl-3-O-methyl-alpha-L-ribo-hexopyranosyl)oxy]-2-fluoro-6-O-methyl-3-oxo-12,11-(oxycarbonyl[((2R)-1-amino-3-hydroxy-2-propyl) imino]]-erythromycin 0.8 g of the product of Stage B, 8 ml of methanol, 315 mg of ammonium formate and 800 mg of palladium on carbon were mixed together and the reaction mixture was refluxed for 4 hours and 30 minutes under hydrogen. The reaction medium was allowed to return to ambient temperature and then was filtered. The filtrate was concentrated under reduced pressure and 660 mg of product which was taken up in 20 ml of ethyl acetate followed by pouring into a 20% solution of ammonium hydroxide. The mixture was stirred followed by decanting and extracting with ethyl acetate, drying and filtering to obtain 660 mg of the desired product.

Stage D: (3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2,6,8(7H,9H)-trione 0.3795 g of the product of the preceding stage, 4 ml of ethanol and 62 µl of acetic acid were refluxed with stirring for 6 days and then was allowed to return to ambient temperature, followed by concentrating under reduced pressure. The residue was taken up in ethyl acetate and the solution was poured into a 20% solution of ammonium hydroxide. The mixture was stirred for 15 minutes followed by decanting, extracting with ethyl acetate, drying, filtering, rinsing and evaporating to obtain 0.304 g of product which was purified by chromatography on silica eluting with a chloroform/isopropanol/ammonium hydroxide mixture (90/10/0.4) to obtain 88 mg of the desired product.

Preparation 1

12-(oxycarbonylimidazol)-11-deoxy-10,11-didehydro-3-de[2,6-dideoxy-3-C-methyl-3-O-methyl-α-L-ribohexopyranosyl)oxy]6-O-methyl-3-oxo-erythromycin 2'-acetoxy 2α-fluoro Stage A: 11-deoxy 10,11-didehydro-3-de[(2,6-dideoxy 3-O-methyl α-L-ribohexopyranosyl)oxy]6-O-methyl-3-oxo-erythromycin.

A mixture of 8.722 g of 11-deoxy 10,11-didehydro 3-de[(2,6-dideoxy 3-O-methyl α-L-ribohexopyranosyl)oxy] 6-O-methyl 3-oxo erythromycin (EP 596 802) 2'-acetate and 350 ml of anhydrous methanol was stirred for 44 hours. The reaction medium was evaporated, taken up with methylene chloride and dried to obtain 8.794 g of the desired product.

Stage B: 11-deoxy 10,11-didehydro-3-de[(2,6-dideoxy 3-O-methyl α-L-ribohexopyranosyl)-oxy]-6-O-methyl 3-oxo erythromycin 2'-trimethylsilyloxy.

A mixture of 3.08 g of the product of Stage A, 340 mg of imidazole, 32 ml of anhydrous THF and 1.06 ml of hexamethyl-disilazane was Stirred at ambient temperature for 4 days. The reaction medium was then evaporated to dryness and the residue was taken up in a mixture of 60 ml of methylene chloride and 60 ml of a 0.5 M aqueous solution of sodium acid phosphate. The mixture was stirred for 15 minutes followed by decanting, extracting with methylene chloride, drying and evaporating to dryness to obtain 3.345 g of the desired product.

Stage C: 11-deoxy 10,11-didehydro 3-de[(2,6-dideoxy 3-O-methyl α-L-ribohexopyranosyl)oxy] 6-O-methyl 3-oxo erythromycin 2'-trimethylsilyloxy 2α-fluoro.

1.24 ml of a solution of potassium terbutylate in 0.97M THF were added at −12≡C, under an argon atmosphere, to a solution of 668 mg of 11-deoxy 10,11-didehydro 3-de[(2,6-dideoxy 3-O-methyl α-L-ribohexopyranosyl)oxy] 6-O-methyl 3-oxo erythromycin 2'-trimethylsilyloxy in 6.7 ml of anhydrous THF. The mixture was stirred for 5 minutes and 378 mg of N-fluoro dibenzenesulfonimide were added followed by stirring for 10 minutes at −12≡C. The mixture was allowed to return to ambient temperature over 90 minutes. Isolation and purification operations were carried out to obtain 695 mg of the desired product.

Stage D: 11-deoxy 10,11-didehydro-3-de[(2,6-dideoxy 3-C-methyl 3-O-methyl α-L-ribohexopyranosyl)-oxy]-6-O-methyl-3-oxo-erythromycin 2α-fluoro.

A mixture of 5.476 g of the product of Stage C, 50 ml of THF and 11.2 ml of 1M tetrabutylammonium fluoride in THF was stirred for 3 hours 30 minutes and the solvent was evaporated off. 37 ml of ethyl acetate, 37 ml of water and 7.5 ml of 20% ammonium hydroxide were added and the mixture was stirred for 10 minutes followed by decanting, extraction with ethyl acetate, drying and filtering. The filtrate was concentrated to dryness and the product was chromatographed on silica eluting with an ammoniated $CH_2Cl_2$-MeOH mixture 99-1, then 98-2, 97-3, 96-4, 95-5 to obtain 2.452 g of the desired product.

Stage E: 11-deoxy 10,11-didehydro 3-de[(2,6-dideoxy 3-O-methyl α-L-ribohexopyranosyl)oxy] 6-O-methyl 3-oxo erythromycin 2'-acetoxy 2α-fluoro.

1.02 g of the product of Stage D, 10 ml of methylene chloride and 241 µl of acetic anhydride were stirred for 3 hours followed by evaporation. Then, 10 ml of water and 10 ml of ethyl acetate were added and the reaction medium stood for 1 hour at ambient temperature with stirring, followed by decanting, drying and evaporating to obtain 1.01 g of the desired product.

Stage F: 12-(oxycarbonylimidazol)-11-deoxy-10,11-didehydro-3-de[(2,6-dideoxy-3-C-methyl-3-O-methyl-α-L-ribo-hexopyranosyl)-oxy]-6-O-methyl-3-oxo-erythromycin-2'-acetoxy-2α-fluoro.

0.388 g of 1,1,'-carbonyldiimidazole and 24 µl of DBU were added at 0≡C to a solution of 1.01 g of the product of Stage E and 10 ml of anhydrous THF and the mixture was stirred at 0° C. for 19 hours. The THF was evaporated off and 10 ml of water and 10 ml of ethyl acetate were added. The reaction mixture was stirred for 10 minutes followed by extracting, drying and evaporating to obtain 0.902 g of the crude sought product which was chromatographed eluting with an ethyl acetate-triethylamine mixture 96-4 to obtain 0.573 g of the desired product.

EXAMPLE 3

(3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2,6,8(7H,9H)-trione Stage A: (3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2,6,8(7H,9H)-trione.

299 mg of the product of Example 2, 3 ml of ethyl acetate and 46 µl of acetic anhydride were stirred at ambient temperature for 20 hours and then was poured into a 20% saturated solution of ammonium hydroxide followed by stirring for 20 minutes, decanting and extracting with ethyl acetate, drying, filtering and evaporating to obtain 0.3296 g of the desired product.

Stage B: (3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2,6,8(7H,9H)-trione A mixture of 180 mg of the product of Stage A, 6 ml of methylene chloride, 137 µl of TEA, 0.142 g of acid chloride and 33.2 mg of DMAP was refluxed for 5 hours 30 minutes and the reaction mixture was then poured into a 10% aqueous solution of ammonium hydroxide followed by decanting. The organic phase was washed with a saturated solution of sodium chloride, water and the aqueous phase was extracted with ethyl acetate. The organic phases were combined, dried, filtered and evaporated to obtain 0.23 g of the crude sought product which was purified by chromatography on silica eluting with a chloroform, isopropyl alcohol, ammonium hydroxide mixture 96-4-0,1%.

Stage C: (3aS,4R,7S,9R,10R,11R,13R,15R,15aR,18S)-4-ethyl-7-fluoro-3a,4,10,11,12,13,15,15a-octahydro-18-(hydroxymethyl)-11-methoxy-3a,7,9,11,13,15-hexamethyl-10-[[3,4,6-trideoxy-3-(dimethylamino)-beta-D-xylo-hexopyranosyl]oxy]-14,1-(nitriloethano)-2H-oxacyclotetradecino[4,3-d]oxazole-2,6,8(7H,9H)-trione A mixture of 0.135 g of the product of Stage B and 2 ml of methanol was stirred for 24 hours followed by evaporating to dryness. The residue was taken up in ethyl acetate. 20 ml of 10% ammonium hydroxide were added. The mixture was stirred for 10 minutes followed by decanting, extracting with ethyl acetate, drying, filtering and evaporating. The residue was taken up in ether, filtered and dried to obtain the desired product with a rf=0.40 $CHCl_3$, MeOH, $NH_4OH$=96-4-0.4, mass spectrum $MH^+$=683$^+$.

Example of Pharmaceutical Composition

Tablets (1 g) containing 150 mg of the Product of Example 1 and sufficient excipient of starch, talc, magnesium stearate were prepared.

Pharmacological Study of the Products of the Invention

Method of Dilutions in Liquid Medium

A series of tubes were prepared in which the same quantity of nutritive sterile medium was distributed. Increasing quantities of the product to be studied were distributed into each tube and then each tube was seeded with a bacterial strain. After incubation for twenty-four hours in an oven at 37° C., the growth inhibition was evaluated by transillumination, which allowed the minimal inhibitory concentrations (M.I.C.) to be determined, expressed in micrograms/ml.

The following results were obtained: (reading after 24 hours)

| GRAM$^+$ bacterial strains | Example 1 | Example 3 |
| --- | --- | --- |
| S. aureus 011UC4 | 0.150 | 0.040 |
| S. aureus 011UC4 + 50% serum | 0.040 | 0.040 |
| S. aureus 011GO25I | 0.600 | 0.040 |
| S. epidermidis 012GO11I | 0.300 | 0.150 |
| S. pyogenes 02A1UC1 | 0.040 | # 0.02 |
| S. agalactiae 02B1HT1 | # 0.02 | 0.02 |
| S. faecalis 02D2UC1 | 0.040 | 0.02 |
| S. faecium 02D3HT1 | # 0.02 | 0.02 |
| Streptococcus gr. G 02GOGR5 | 0.040 | 0.02 |
| S. mitis 02MitCB1 | 0.040 | 0.02 |
| S. agalactiae 02B1SJ1c | 1.200 | 0.02 |
| S. pneumoniae 032UC1 | 0.080 | 0.02 |
| S. pneumoniae 030GR20 | # 0.02 | 0.02 |

Moreover, the product of Example 1 showed a useful activity on the following Gram$^-$ bacterial strains: *Haemophilus Influenzae* 351HT3, 351CB12 and 351CA1.

Various modifications of the products of the invention may be made without departing from the spirit or scope thereof and it is to be understood that the invention is intended to be limited only as defined in the appended claims.

The invention claimed is:

1. A process for the preparation of a compound of formula (I):

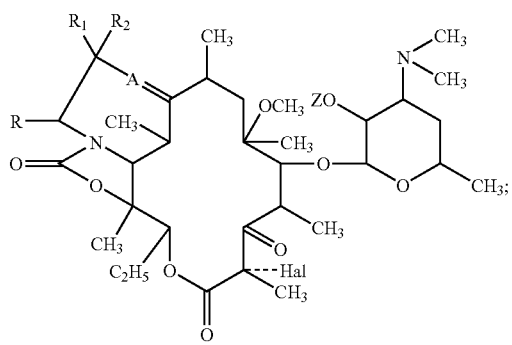

wherein:
A is nitrogen or N→O;
Hal is halogen;
$R_1$ and $R_2$ are the same or different and are independently chosen from hydrogen or $C_1$–$C_{18}$alkyl;
R is —$(CH_2)_m$OB; wherein
  m is an integer from 1 to 8; and
  B is hydrogen, —COAr or —$(CH_2)_n$—Ar; wherein
    n is an integer from 1 to 8; and
    Ar is a mono- or polycyclic aryl or heteroaryl;
Z is hydrogen or $C_1$–$C_{18}$-acyl;
said process comprising:
reacting a compound of formula (IIIA)

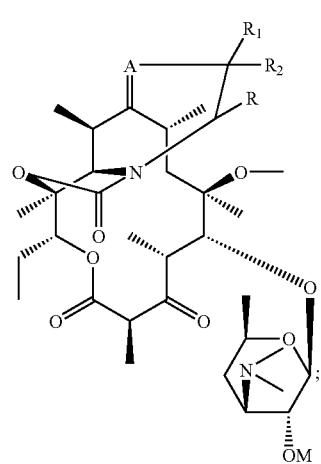

wherein:
A, R, $R_1$ and $R_2$ are as defined above; and
M is a hydroxyl protecting group;

with a suitable halogenating agent to obtain a compound of the formula IB:

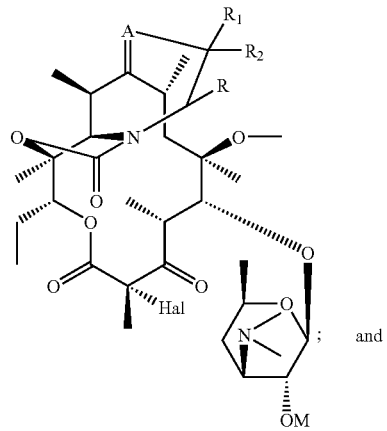

reacting the compound of formula (IB) with a suitable deprotecting agent to obtain the compound of formula (I) wherein Z is hydrogen.

2. The process as set forth in claim 1, further comprising reacting the compound of formula (I) wherein Z is hydrogen with a suitable esterification agent to obtain the compound of formula (I) wherein Z is $C_1$–$C_{18}$-acyl.

3. The process as set forth in claim 1, further comprising reacting the compound of formula (I) wherein Z is hydrogen with a suitable acid to form the corresponding acid addition salt of the compound of formula (I) wherein Z is hydrogen.

4. The process as set forth in claim 2, further comprising reacting the compound of formula (I) wherein Z is $C_1$–$C_{18}$-acyl with a suitable acid to form the corresponding acid addition salt of the compound of formula (I) wherein Z is $C_1$–$C_{18}$-acyl.

5. The process as set forth in claim 1, wherein M is trimethylsilyl group.

6. The process as set forth in claim 1, wherein said halogenation is carried out in the presence of potassium tert-butoxide.

7. The process as set forth in claim 1, wherein said halogenating agent is of the formula:

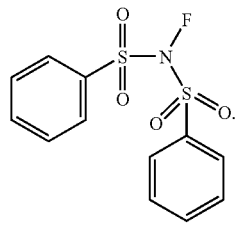

* * * * *